(12) United States Patent
Alshawi et al.

(10) Patent No.: US 10,213,274 B1
(45) Date of Patent: Feb. 26, 2019

(54) METHOD OF TRACKING AND NAVIGATION FOR A DENTAL INSTRUMENT

(71) Applicant: KING SAUD UNIVERSITY, Riyadh (SA)

(72) Inventors: Tariq Abdulrahman Alshawi, Riyadh (SA); Asma'A Abdurrahman Al-Ekrish, Riyadh (SA); Saleh Abdullah Alshebeili, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 15/918,853

(22) Filed: Mar. 12, 2018

(51) Int. Cl.
*A61B 34/20* (2016.01)
*A61C 1/08* (2006.01)
*A61B 90/00* (2016.01)

(52) U.S. Cl.
CPC .............. *A61C 1/082* (2013.01); *A61B 34/20* (2016.02); *A61B 90/39* (2016.02); *A61B 2090/3904* (2016.02); *A61B 2090/3945* (2016.02)

(58) Field of Classification Search
CPC ..................... A61B 34/30; A61B 2090/3983
USPC ....................................................... 702/150
See application file for complete search history.

(56) References Cited

U.S. PATENT DOCUMENTS

| 6,978,167 B2 | 12/2005 | Dekel et al. | |
|---|---|---|---|
| 8,435,033 B2 | 5/2013 | Gross et al. | |
| 9,566,123 B2 | 2/2017 | Daon | |
| 2007/0211081 A1* | 9/2007 | Quadling | A61C 13/0004 345/632 |
| 2010/0210943 A1* | 8/2010 | Mahmoud | A61B 8/14 600/437 |
| 2014/0178832 A1 | 6/2014 | Choi et al. | |
| 2015/0216541 A1 | 8/2015 | Schmieding et al. | |
| 2016/0067007 A1* | 3/2016 | Piron | A61B 5/7246 705/3 |
| 2016/0157815 A1 | 6/2016 | Slak et al. | |
| 2016/0166333 A1* | 6/2016 | Wang | A61B 34/10 600/476 |
| 2016/0235483 A1 | 8/2016 | Zeilhofer et al. | |
| 2016/0324598 A1 | 11/2016 | Bothorel et al. | |
| 2016/0345858 A1* | 12/2016 | Tromberg | A61B 5/067 |

(Continued)

FOREIGN PATENT DOCUMENTS

| WO | 2016082018 A1 | 6/2016 |
|---|---|---|
| WO | 2016154557 A1 | 9/2016 |

OTHER PUBLICATIONS

Bordin et al., "Deconstructed Science: Dynamic Navigation in Implant Dentistry," printed from http://www.trendsperioimplantresourcecenter.com/content/dynamic-navigation-implant-dentistry on Oct. 3, 2017; 15 pages.

*Primary Examiner* — Yoshihisa Ishizuka
(74) *Attorney, Agent, or Firm* — Richard C. Litman

(57) ABSTRACT

The method of tracking and navigation for a dental instrument uses feature extraction, a feature space transformation and a fusion procedure to detect the location of a target, such as a marker placed on a patient's jaw, as well as detecting the location of a dental instrument with respect to the target for guiding a dental practitioner during a procedure. Detection is performed by identifying potential locations for the target and then refining the potential locations based on information from previous detection frames. Given an initial estimate of the target's three-dimensional location, the estimate is improved through iteratively updated information.

1 Claim, 2 Drawing Sheets

(56) References Cited

U.S. PATENT DOCUMENTS

| | | |
|---|---|---|
| 2017/0209225 A1 | 7/2017 | Wu |
| 2017/0231718 A1 | 8/2017 | Wohrle et al. |
| 2017/0281280 A1* | 10/2017 | Haider .................. A61B 34/20 |
| 2017/0312049 A1 | 11/2017 | Nielsen et al. |
| 2018/0055579 A1* | 3/2018 | Daon ..................... A61C 1/082 |

* cited by examiner

METHOD OF TRACKING AND NAVIGATION FOR A DENTAL INSTRUMENT

BACKGROUND

1. Field

The disclosure of the present patent application relates to machine vision-based navigation and tracking, and particularly to a method of tracking and navigation for dental instruments during dental procedures.

2. Description of the Related Art

Accurate drilling and placement of dental implants is crucial to avoid encroaching upon vital anatomic structures and for the success of dental implant procedures. The size, position and orientation of dental implants may be planned based upon the computed tomography (CT) images of a patient's jaw bone. During dental surgery, deviation from the planned entry point, angle or depth may result in nerve damage, critical bleeding, persistent numbness, discomfort to the patient or failure of the implant therapy, and ultimately might require further surgical intervention.

It is common for dental surgeons to rely on surgical stents (i.e., a thermoplastic mold which allows precise and narrow entry of the drill bur) to improve the accuracy of the surgery. However, in many cases, using surgical stents might not be feasible or convenient to the surgeon, who might rely on free hand surgery, which is obviously prone to human error. A wide variety of mechanical surgical guides are known, but most do not provide the comfort of free hand surgery.

Although machine vision-based tracking has been used, the markers used in such systems are typically cumbersome and are not made easily compatible with the dental instruments. More importantly, simple machine vision-based tracking, which relies on a basic camera detector for identifying the marker, without any further processing or feature identification, is prone to identification errors, blocking of the cameras and/or markers, and detection noise. Since even a minor deviation in the surgical procedure can be harmful for the patient, the machine vision-based tracking procedure must be as accurate and error free as possible. Thus, a method of tracking and navigation for a dental instrument solving the aforementioned problems is desired.

SUMMARY

The method of tracking and navigation for a dental instrument uses feature extraction, a feature space transformation and a fusion procedure to detect the location of a target, such as a marker placed on a patient's jaw, as well as detecting the location of a dental instrument with respect to the target for guiding a dental practitioner during a procedure. Detection is performed by identifying potential locations for the target and then refining the potential locations based on information from previous detection frames. Given an initial estimate of the target's three-dimensional location, the estimate is improved through iteratively updated information.

Initially, a set of spatiotemporal marker tensors, $T_j$, where $j=1, \ldots, M$, are established. As in a conventional procedure, a tomographic image of an area of interest of the patient is produced and displayed on a conventional display to the dental practitioner. A plurality of the patient tracking markers are positioned on the patient in the area of interest, such as in the patient's jaw, and a plurality of instrument tracking markers are positioned on a dental instrument. The total number of the patient tracking markers and the instrument tracking markers is represented as M. A set of spatiotemporal sensor tensors, $I_h$, where $h=1, \ldots, K$, are established, where K represents the number of visual sensors.

A singular value decomposition is performed on each of the spatiotemporal marker tensors to produce a corresponding pair of orthogonal tensors, $\mathcal{U}$ and $\mathcal{V}$, and a corresponding singular values diagonal tensor, $\mathcal{S}$, where $\mathcal{S}(a, b, c)$ represents a point in the diagonal tensor $\mathcal{S}$ corresponding to a set of three-dimensional indices, $(a, b, c)$. From $\mathcal{U}$ and $\mathcal{V}$, an $l^{th}$ feature space basis, $B_F^{(l)}$, is calculated as $B_F^{(l)} = [\mathcal{U}(a+r_1^u, b+r_2^u, c+r_3^u) | \mathcal{V}(a+r_1^v, b+r_2^v, c+r_3^v)]$, where $l=1, \ldots, L$. Here, L represents a total number of feature space bases; $r_1^u, r_2^u, r_3^u, r_1^v, r_2^v, r_3^v$ are each predetermined ranges of values; and $\mathcal{S}(a, b, c)$ is greater than a first threshold value, $Threshold_1$. The first threshold value, $Threshold_1$, is determined empirically.

An $l^{th}$ extracted feature tensor, $F_h^{(l)}$, is then calculated as $F_h^{(l)} = I_h \circledast B_F^{(l)}$, where $l=1, \ldots, L$ and $h=1, \ldots, K$. From the extracted feature tensors, an $l^{th}$ saliency map, $SM_h^{(l)}$, can be calculated for each extracted feature tensor, $F_h^{(l)}$, as $SM_h^{(l)} = FFT2\{|FFT2\{FFT2\{F_h^{(l)}(t)\}\}|\}$, where $l=1, \ldots, L$ and $h=1, \ldots, K$, FFT2 represents a two-dimensional fast Fourier transform, and t represents time.

From the set of saliency maps, an $l^{th}$ uncertainty map, $UM_h^{(l)}$, is calculated for each saliency map, $SM_h^{(l)}$, as:

$$UM_h^{(l)} = SM_h^{(l)} \cdot P[SM_h^{(l)}(a,b,c) > Threshold_2 | \{I_1, I_2, \ldots, I_K\}, \{T_1, T_2, \ldots, T_M\}],$$

where $P[.]$ represents a probability of a pixel $(a, b, c)$ of saliency map $SM_h^{(l)}$ being above a second threshold value, $Threshold_2$. The second threshold value, $Threshold_2$, is determined empirically. A fused saliency map, FSM, is then calculated as:

$$FSM = \sum_{h=1}^{K} \sum_{l=1}^{L} \frac{\sum UM_h^{(l)}}{\prod UM_h^{(l)}} SM_h^{(l)},$$

and from this, a binary fused map, $FSM^b$, is calculated as $FSM^b = FSM$ when FSM is greater than a third threshold value, $Threshold_3$. The third threshold value, $Threshold_3$, is also determined empirically.

The binary fused map is overlaid on the tomographic image to provide visual feedback of the dental instrument relative to the area of interest of the patient on a display. The above occurs for a single frame at one point in time. Thus, the method returns to the step of performing singular value decomposition on each of the spatiotemporal marker tensors for the next frame.

These and other features of the present invention will become readily apparent upon further review of the following specification.

DETAILED DESCRIPTION OF THE PREFERRED EMBODIMENTS

Figure 1:
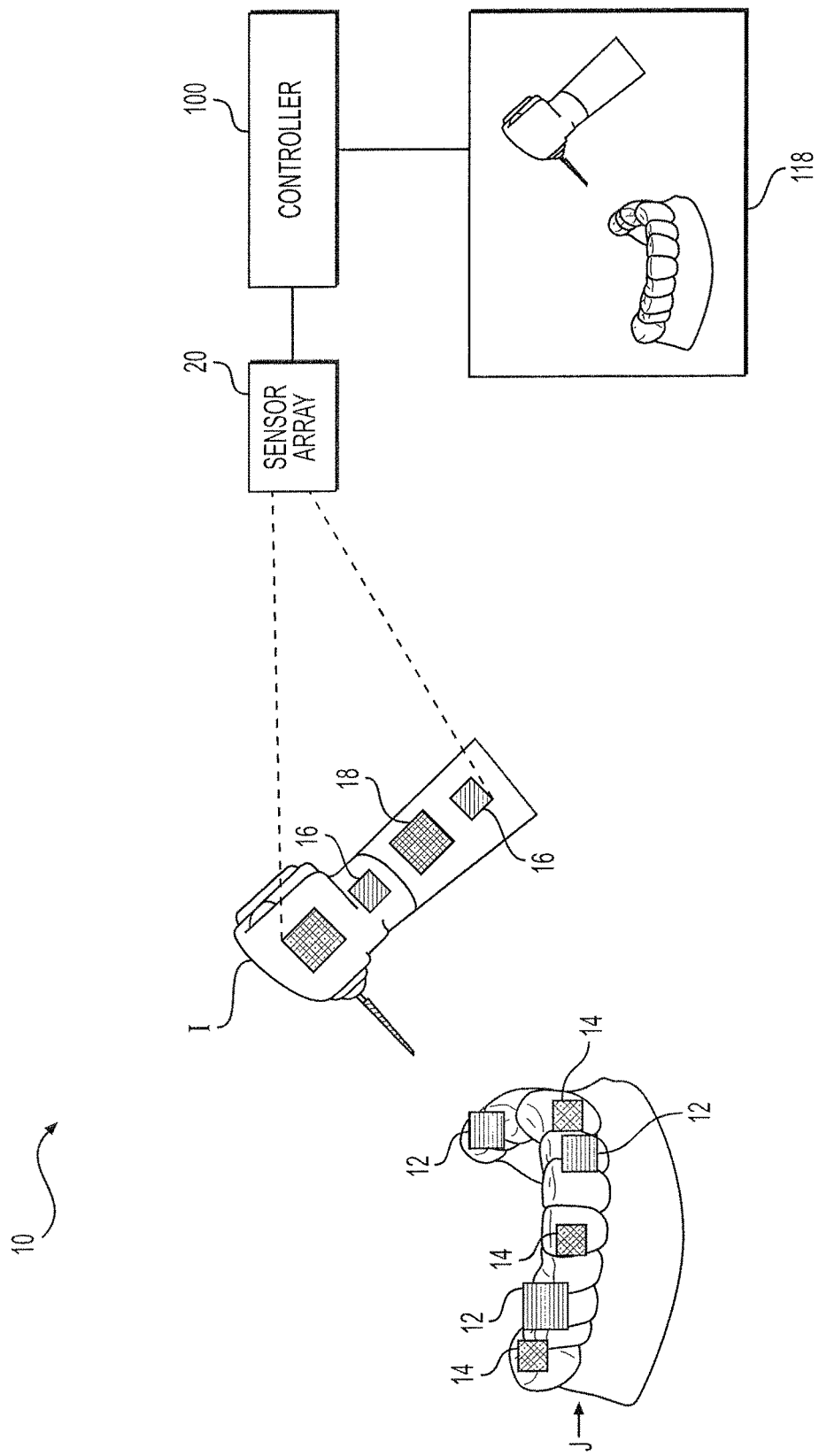
FIG. 1 is a schematic diagram illustrating implementation of a method of tracking and navigation for a dental instrument

The method of tracking and navigation for a dental instrument uses feature extraction, a feature space transformation and a fusion procedure to detect the location of a target, such as a marker placed on a patient's jaw, as well as detecting the location of a dental instrument with respect to the target for guiding a dental practitioner during a procedure. As shown in the example of FIG. 1, the overall system 10 includes a plurality of patient tracking markers 12, 14 placed at various desired locations on the patient's jaw J. It should be understood that the positioning of the markers 12, 14 in FIG. 1 is shown for exemplary purposes only, and actual positioning is ultimately dependent upon the types of markers used, the patient's jaw structure, and the particular dental procedure. Similarly, a plurality of instrument tracking markers 16, 18 are positioned on a dental instrument I. It should be understood that the dental instrument I is also shown for exemplary purposes only.

As shown in FIG. 1, one or more different types of markers may be used. As an example, both active patient tracking markers 12 and passive patient tracking markers 14 are applied to the patient's jaw J in the example of FIG. 1. Similarly, both active instrument tracking markers 16 and passive instrument tracking markers 18 may be applied to the instrument I. Active markers interactively change status with respect to time. For example, light emitting diode (LED) panels may be used as active markers, a pre-programmed pattern of blinking by the LED panels being used for detection by a sensor array 20. In an active marker system, the sensor array 20 could detect the active markers by illumination characteristics and/or time-variability in the displayed pattern. It should be understood that any suitable type of active markers may be utilized, such as infrared LEDs. Passive markers are unchanging markers, such as barcodes, matrix barcodes, or any other visually recognizable tag based on, for example, structure and/or color. Although active markers 12, 16 provide for more reliable detection by the sensor array 20, passive markers 14, 18 may be used, either alone or in combination therewith, to reduce cost and/or provide redundancy and additional reliability during machine vision detection.

Detection is performed by identifying potential locations for the target and then refining the potential locations based on information from previous detection frames. Given an initial estimate of the target's three-dimensional location, the estimate is improved through iteratively updated information. Markers 12, 14, 16, 18 are detected by the sensor array 20, which may be any suitable type of sensor array, such as one or more visible light RGB cameras, infrared cameras, infrared sensors, multi-spectral cameras, or the like.

Initially, a set of spatiotemporal marker tensors, $T_j$, where $j=1, \ldots, M$, are established. It should be noted that the spatiotemporal markers are established before the procedure begins, as they are related to the markers themselves. Thus, the set of spatiotemporal marker tensors, $T_j$, is fixed for all patients and all subsequent procedures, so long as the same set of spatiotemporal markers are used. As in a conventional procedure, a tomographic image of an area of interest of the patient is produced and displayed to the dental practitioner on a conventional display 118.

A plurality of the patient tracking markers 12, 14 are positioned on the patient in the area of interest, such as in the patient's jaw J, and a plurality of instrument tracking markers 16, 18 are positioned on the dental instrument I. The total number of the patient tracking markers 12, 14 and instrument tracking markers 16, 18 is represented as M. A set of spatiotemporal sensor tensors, $I_h$, where $h=1, \ldots, K$, are established, where K represents a number of visual sensors (i.e., the number of sensors forming sensor array 20).

A singular value decomposition is performed on each of the spatiotemporal marker tensors to produce a corresponding pair of orthogonal tensors, $\mathcal{U}$ and $\mathcal{V}$, and a corresponding singular values diagonal tensor, $\mathcal{S}$, where $\mathcal{S}$ (a, b, c) represents a point in the diagonal tensor $\mathcal{S}$ corresponding to a set of three-dimensional indices, (a, b, c). From $\mathcal{U}$ and $\mathcal{V}$, an $l^{th}$ feature space basis, $B_F^{(l)}$, is calculated as $B_F^{(l)}=[\mathcal{U}(a+r_1^u, b+r_2^u, c+r_3^u)|\mathcal{V}(a+r_1^v, b+r_2^v, c+r_3^v)]$, where $l=1, \ldots, L$. Here, L represents a total number of feature space bases, $r_1^u, r_2^u, r_3^u, r_1^v, r_2^v, r_3^v$ are each predetermined ranges of values, and $\mathcal{S}$ (a, b, c) is greater than a first threshold value, $Threshold_1$. The first threshold value, $Threshold_1$, is determined empirically.

An $l^{th}$ extracted feature tensor, $F_h^{(l)}$, is then calculated as $F_h^{(l)} = I_h \circledast B_F^{(l)}$, where $l=1, \ldots, L$ and $h=1, \ldots, K$. From the extracted feature tensors, an $l^{th}$ saliency map, $SM_h^{(l)}$, can be calculated for each extracted feature tensor, $F_h^{(l)}$, as:

$$SM_h^{(l)}(t) = FFT2\{|FFT2\{FFT2\{F_h^{(l)}(t)\}\}|\},$$

where $l=1, \ldots, L$ and $h=1, \ldots, K$, FFT2 represents a two-dimensional fast Fourier transform, and t represents time. It should be noted that in this step, one three-dimensional tensor (i.e., the $l^{th}$ extracted feature tensor, $F_h^{(l)}$) is being transformed into another three-dimensional tensor (i.e., the $l^{th}$ saliency map, $SM_h^{(l)}$), which is performed via the two-dimensional fast Fourier transform iterated over time t. Thus, the time, t, represented above is the iteration variable used in this transformation step.

From the set of saliency maps, an $l^{th}$ uncertainty map, $UM_h^{(l)}$, is calculated for each saliency map, $SM_h^{(l)}$, as:

$$UM_h^{(l)} = SM_h^{(l)} \cdot P[SM_h^{(l)}(a,b,c) > Threshold_2 | \{I_1, I_2, \ldots, I_K\}, \{T_1, T_2, \ldots, T_M\}],$$

where P[.] represents a probability of a pixel (a, b, c) of saliency map $SM_h^{(l)}$ being above a second threshold value, $Threshold_2$. The second threshold value, $Threshold_2$, is determined empirically. A fused saliency map, FSM, is then calculated as:

$$FSM = \sum_{h=1}^{K} \sum_{l=1}^{L} \frac{\sum UM_h^{(l)}}{\prod UM_h^{(l)}} SM_h^{(l)},$$

and from this, a binary fused map, $FSM^b$, is calculated as $FSM^b = FSM$ when FSM is greater than a third threshold value, $Threshold_3$. The third threshold value, $Threshold_3$, is also determined empirically.

The binary fused map is overlaid on the tomographic image to provide visual feedback of the dental instrument I relative to the area of interest J of the patient on the display 118. Here, the process of overlaying the binary fused map may be accomplished using any suitable technique, such as a direct overlaying, or by calculating a number of pixels between the calculated map representations of the patient tracking markers 12, 14 and the instrument tracking markers 16, 18. A pixel-to-real-world-distance transform function (which may be obtained during calibration) can then be used to estimate the distance between the instrument I and the patient's jaw J, which may then be visually displayed on the tomographic image and/or represented as numbers on the display 118. The above occurs for a single frame at one point in time. Thus, the method returns to the step of performing singular value decomposition on each of the spatiotemporal marker tensors for the next frame.

Figure 2:
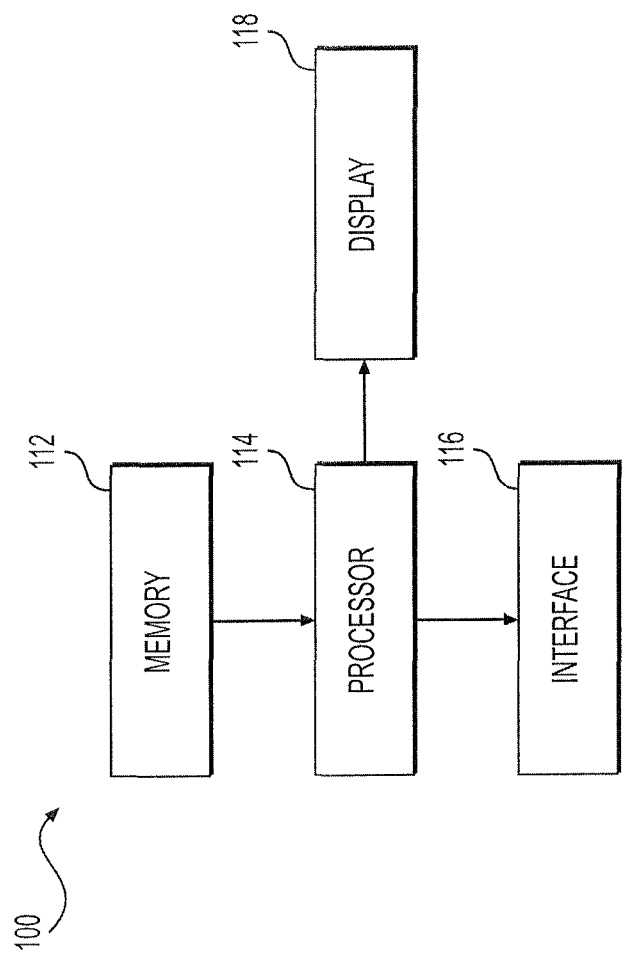
FIG. 2 is a block diagram illustrating components of a controller for implementing the method of tracking and navigation for a dental instrument.

It should be understood that the calculations may be performed by any suitable computer system, such as that diagrammatically shown in FIG. 2. Data is entered into a controller 100 via any suitable type of user interface 116, and may be stored in memory 112, which may be any suitable type of computer readable and programmable memory and is preferably a non-transitory, computer readable storage medium. Calculations are performed by a processor 114, which may be any suitable type of computer processor and may be displayed to the user on the display 118, which may be any suitable type of computer display.

The processor 114 may be associated with, or incorporated into, any suitable type of computing device, for example, a personal computer or a programmable logic controller. The display 118, the processor 114, the memory 112 and any associated computer readable recording media are in communication with one another by any suitable type of data bus, as is well known in the art.

Examples of computer-readable recording media include non-transitory storage media, a magnetic recording apparatus, an optical disk, a magneto-optical disk, and/or a semiconductor memory (for example, RAM, ROM, etc.). Examples of magnetic recording apparatus that may be used in addition to memory 112, or in place of memory 112, include a hard disk device (HDD), a flexible disk (FD), and a magnetic tape (MT). Examples of the optical disk include a DVD (Digital Versatile Disc), a DVD-RAM, a CD-ROM (Compact Disc-Read Only Memory), and a CD-R (Recordable)/RW. It should be understood that non-transitory computer-readable storage media include all computer-readable media, with the sole exception being a transitory, propagating signal.

It is to be understood that the method of tracking and navigation for a dental instrument is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of tracking and navigation for a dental instrument to assist a dental practitioner during a procedure on a patient with the aid of a computer system, comprising the steps of:

establishing a fixed set of spatiotemporal marker tensors for the patient, $T_j$, where $j=1, \ldots, M$;

producing a tomographic image of an area of interest of the patient, wherein the tomographic image is configured to be displayed to the dental practitioner;

providing the computer system, wherein the computer system includes at least a memory and a processor;

positioning a plurality of patient tracking markers on the patient in the area of interest, wherein the step of positioning the plurality of patient tracking markers on the patient in the area of interest comprises positioning a plurality of active and passive patient tracking markers on the patient in the area of interest;

positioning a plurality of instrument tracking markers on a dental instrument, wherein the step of positioning the plurality of instrument tracking markers on the dental instrument comprises positioning a plurality of active and passive instrument tracking markers on the dental instrument and defining visual sensors, M being a combined number of the positioned patient and instrument tracking markers;

providing the computer system, wherein the computer system includes at least a memory and a processor configured to perform the steps of:

a) establishing a set of spatiotemporal sensor tensors, $I_h$, where $h=1, \ldots, K$, K being a number of visual sensors deployed for detecting the patient and instrument tracking markers, wherein the deployed visual sensors define a sensor array;

b) performing singular value decomposition on each of the spatiotemporal marker tensors to produce a corresponding pair of orthogonal tensors, $\mathcal{U}$ and $\mathcal{V}$, and a corresponding singular values diagonal tensor, $\mathcal{S}$, where $\mathcal{S}(a, b, c)$ represents a point in the diagonal tensor $\mathcal{S}$ corresponding to a set of three-dimensional indices, $(a, b, c)$;

c) calculating an $l^{th}$ feature space basis, $B_F^{(l)}$, as $B_F^{(l)} = [\mathcal{U}(a+r_1^u, b+r_2^u, c+r_3^u)| \mathcal{V}(a+r_1^v, b+r_2^v, c+r_3^v)]$, where $l=1, \ldots, L$, and where L represents a total number of feature space bases, $r_1^u, r_2^u, r_3^u, r_1^v, r_2^v, r_3^v$ are each predetermined ranges of values, and $\mathcal{S}(a, b, c)$ is greater than a first threshold value, $Threshold_1$;

d) calculating an $l^{th}$ extracted feature tensor, $F_h^{(l)}$, as $F_h^{(l)} = I_h \circledast B_F^{(l)}$, wherein $l=1, \ldots, L$ and $h=1, \ldots, K$;

e) calculating an $l^{th}$ saliency map, $SM_h^{(l)}$ for each extracted feature tensor, $F_h^{(l)}$ as $SM_h^{(l)} = FFT2\{|FFT2\{FFT2\{F_h^{(l)}(t)\}\}|\}$, where $l=1, \ldots, L$ and $h=1, \ldots, K$, and FFT2 represents a two-dimensional fast Fourier transform;

f) calculating an $l^{th}$ uncertainty map, $UM_h^{(l)}$ for each saliency map, $SM_h^{(l)}$ as $UM_h^{(l)} = UM_h^{(l)} = SM_h^{(l)} - P[SM_h^{(l)}(a, b, c) > Threshold_2|\{I_1, I_2, \ldots, I_K\}, \{T_1, T_2, \ldots, T_M\}]$, where $P[.]$ represents a probability of a pixel $(a, b, c)$ of the saliency map $SM_h^{(l)}$ being above a second threshold value, $Threshold_2$;

g) calculating a fused saliency map, FSM, as $$FSM = \sum_{h=1}^{K} \sum_{l=1}^{L} \frac{\sum UM_h^{(l)}}{\prod UM_h^{(l)}} SM_h^{(l)};$$

h) calculating a binary fused map, $FSM^b$, as $FSM^b = FSM$ when FSM is greater than a third threshold value, $Threshold_3$; and i) constantly providing the computer system with the results of each of the calculations and repetitively recalculating the location of the dental instrument;

overlaying the binary fused map on the tomographic image to provide visual feedback of the dental instrument relative to the area of interest of the patient on a display; and repetitively returning to the step of performing singular value decomposition on each of the spatiotemporal marker tensors, wherein distance between the spatiotemporal marker tensors can then be computed by recalculating the point in the diagonal tensor S corresponding to a set of three-dimensional indices, (a, b, c).

* * * * *